US011779811B2

(12) United States Patent
Kwatra et al.

(10) Patent No.: US 11,779,811 B2
(45) Date of Patent: Oct. 10, 2023

(54) COGNITIVE BASED AUGMENTED REALITY WORKOUT

(71) Applicant: INTERNATIONAL BUSINESS MACHINES CORPORATION, Armonk, NY (US)

(72) Inventors: Shikhar Kwatra, Raleigh, NC (US); Jeremy R. Fox, Georgetown, TX (US); Sushain Pandit, Austin, TX (US); Paul Krystek, Highland, NY (US)

(73) Assignee: International Business Machines Corporation, Armonk, NY (US)

( * ) Notice: Subject to any disclaimer, the term of this patent is extended or adjusted under 35 U.S.C. 154(b) by 493 days.

(21) Appl. No.: 16/918,356

(22) Filed: Jul. 1, 2020

(65) Prior Publication Data
US 2022/0001238 A1   Jan. 6, 2022

(51) Int. Cl.
G06F 3/048 (2013.01)
A63B 24/00 (2006.01)
G06T 19/00 (2011.01)
A61B 5/16 (2006.01)

(52) U.S. Cl.
CPC .......... A63B 24/0075 (2013.01); A61B 5/165 (2013.01); A63B 24/0062 (2013.01); G06T 19/006 (2013.01); *A63B 2024/0068* (2013.01)

(58) Field of Classification Search
CPC ............ A63B 24/0075; A63B 24/0062; A63B 2024/0068; A61B 5/165; G06T 19/006
See application file for complete search history.

(56) References Cited

U.S. PATENT DOCUMENTS

| 6,152,856 | A | 11/2000 | Studor |
| 6,409,599 | B1 | 6/2002 | Sprout |
| 6,902,513 | B1 | 6/2005 | McClure |
| 7,972,247 | B2 | 7/2011 | Daikeler |
| 9,135,347 | B2 * | 9/2015 | Damman ............... G06Q 10/10 |

(Continued)

FOREIGN PATENT DOCUMENTS

WO   2005074542 A2   8/2005

OTHER PUBLICATIONS

Mell et al., "The NIST Definition of Cloud Computing", National Institute of Standards and Technology, Special Publication 800-145, Sep. 2011, pp. 1-7.

*Primary Examiner* — David Phantana-angkool
(74) *Attorney, Agent, or Firm* — Robert D. Bean

(57) ABSTRACT

A method, a computer program product, and a computer system determine a customized augmented reality workout based on a cognitive state of a user. The method includes determining a current cognitive score of the user based on physical descriptions. The method includes determining the cognitive state of the user based on the current cognitive score. The cognitive state is indicative of a stress level being experienced by the user. The method includes determining the customized augmented reality workout from a plurality of augmented reality workouts based on the cognitive state of the user. The method includes generating the customized augmented reality workout to include at least one virtual component and incorporating at least one feature of real world surroundings. The method includes presenting the customized augmented reality workout to the user via an augmented reality device worn by the user.

20 Claims, 6 Drawing Sheets

(56) References Cited

U.S. PATENT DOCUMENTS

| | | |
|---|---|---|
| 10,715,759 B2 * | 7/2020 | Dibenedetto .......... A63F 13/211 |
| 10,814,170 B2 * | 10/2020 | Wang ...................... G16H 20/30 |
| 11,541,278 B2 * | 1/2023 | McKenna ............... G16H 40/63 |
| 2006/0040793 A1 | 2/2006 | Martens |
| 2006/0122035 A1 | 6/2006 | Felix |
| 2007/0225118 A1 | 9/2007 | Giorno |
| 2009/0233769 A1 | 9/2009 | Pryor |
| 2013/0296043 A1 | 11/2013 | Weinshanker |
| 2015/0049114 A1 | 2/2015 | Geisner |
| 2016/0346612 A1 | 12/2016 | Rowley |
| 2017/0173394 A1 * | 6/2017 | Rider .................. A63B 24/0075 |
| 2017/0251160 A1 * | 8/2017 | Dibenedetto ........ A63B 69/002 |
| 2017/0354845 A1 * | 12/2017 | Williams ................. A61B 5/11 |
| 2017/0354846 A1 * | 12/2017 | Von Rueckmann ... G16H 50/50 |
| 2018/0036591 A1 * | 2/2018 | King ........................ H04N 5/76 |
| 2018/0116609 A1 | 5/2018 | Kaleal, III |
| 2019/0065970 A1 * | 2/2019 | Bonutti .................. G06N 5/045 |
| 2020/0245954 A1 * | 8/2020 | Kaleal .................. A61B 5/0205 |
| 2021/0008413 A1 * | 1/2021 | Asikainen .......... A63B 24/0087 |
| 2021/0128978 A1 * | 5/2021 | Gilstrom ............ A63B 71/0619 |
| 2021/0173480 A1 * | 6/2021 | Osterhout ............. G06F 3/0227 |
| 2021/0197026 A1 * | 7/2021 | Kerslake .................. G09B 5/06 |
| 2022/0001238 A1 * | 1/2022 | Kwatra .................... G06F 3/011 |
| 2022/0036891 A1 * | 2/2022 | Zweig .................... G16H 50/30 |
| 2022/0176226 A1 * | 6/2022 | Giudici .............. A63B 71/0622 |
| 2022/0296966 A1 * | 9/2022 | Asikainen ............... G16H 20/30 |
| 2023/0069758 A1 * | 3/2023 | Rao .................... A63B 71/0622 |

* cited by examiner

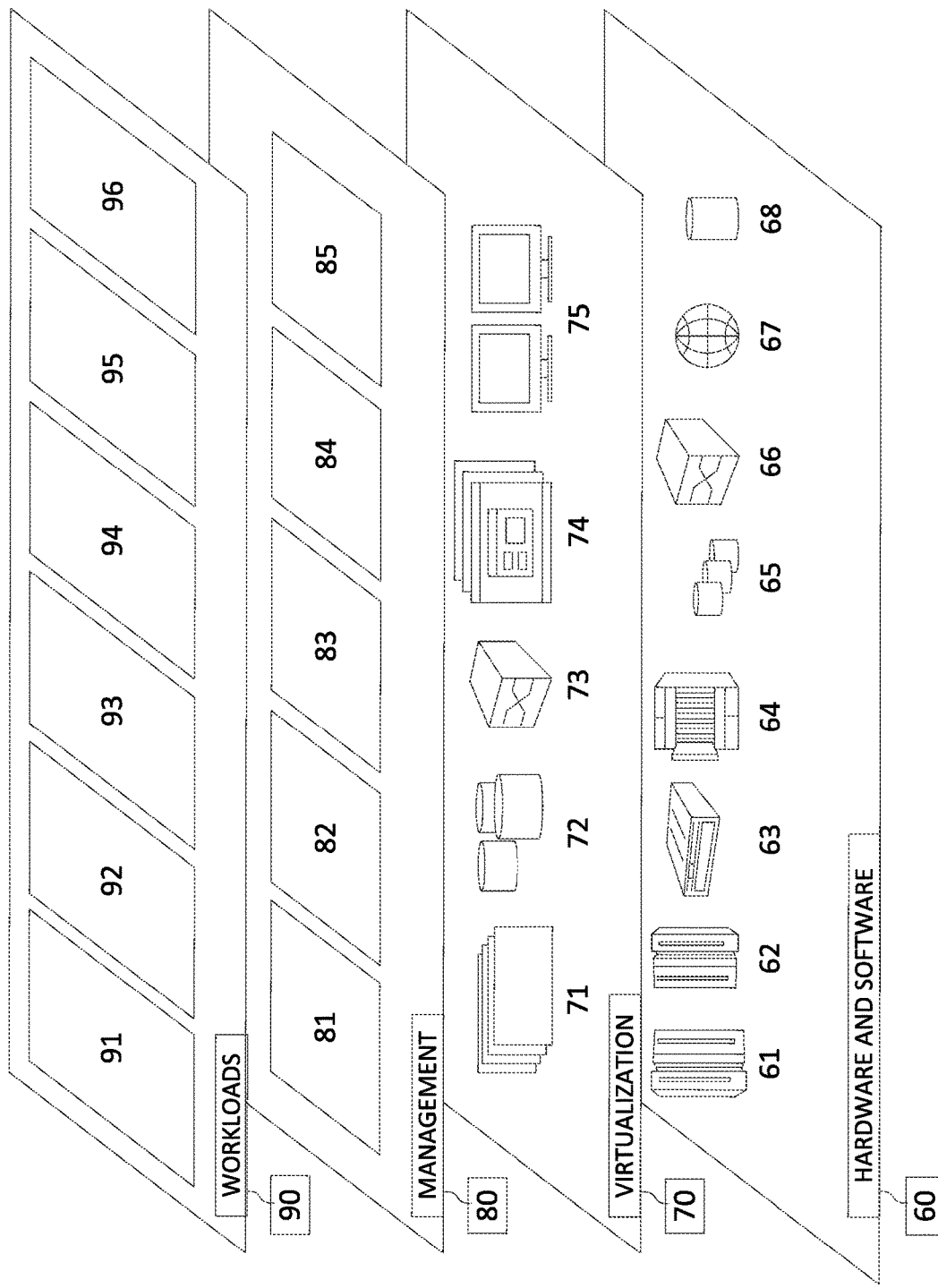

COGNITIVE BASED AUGMENTED REALITY WORKOUT

BACKGROUND

The exemplary embodiments relate generally to augmented reality, and more particularly to measuring a cognitive state of a user to dynamically generate an augmented reality workout.

Augmented reality applications enable a blending of virtual reality components with real world surroundings. For example, a user may wear an augmented reality display that is configured to show the real world surroundings (e.g., through a transparency of the display) as well as include the virtual reality components as if actually interacting with the real world surroundings. In this manner, the augmented reality applications may create images that integrate with contents in the real world as experienced by the user. While using the augmented reality applications, the user may interact with the virtual contents in the real world while maintaining a capability to distinguish between the virtual components and the real world surroundings. Further implementations of the augmented reality applications may enable visualization through virtual components in a wide variety of manners. However, these applications rely on pre-defined rules for the environment and changes that may appear as being dynamic are actually rules based formulas for a sequence of events that are scheduled or preconfigured.

SUMMARY

The exemplary embodiments disclose a method, a computer program product, and a computer system for determining a customized augmented reality workout based on a cognitive state of a user. The method comprises determining a current cognitive score of the user based on physical descriptions. The method comprises determining the cognitive state of the user based on the current cognitive score. The cognitive state is indicative of a stress level being experienced by the user. The method comprises determining the customized augmented reality workout from a plurality of augmented reality workouts based on the cognitive state of the user. The method comprises generating the customized augmented reality workout to include at least one virtual component and incorporating at least one feature of real world surroundings. The method comprises presenting the customized augmented reality workout to the user via an augmented reality device worn by the user.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which:

FIG. 6 depicts abstraction model layers, in accordance with the exemplary embodiments.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
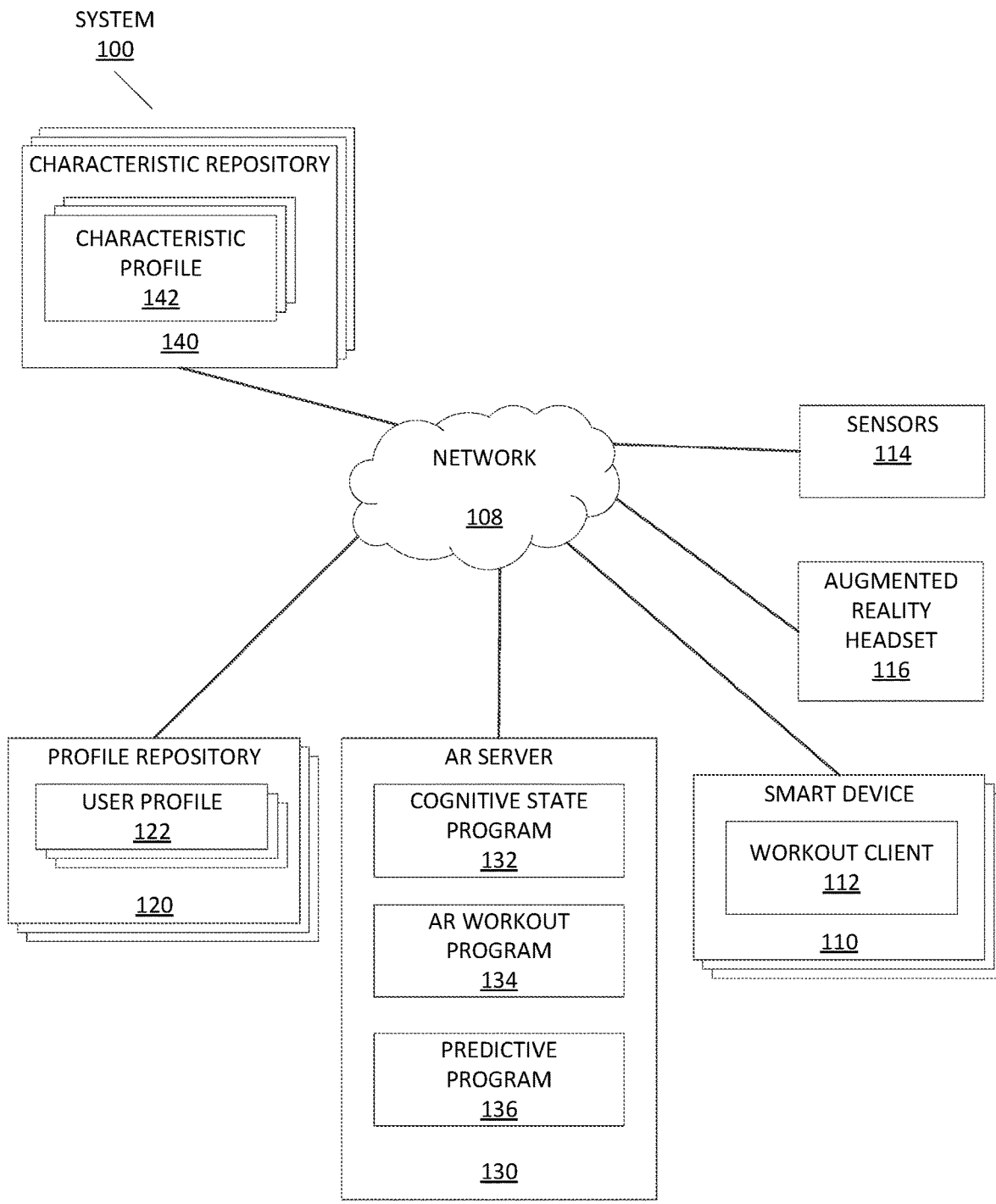
FIG. 1 depicts an exemplary schematic diagram of an augmented reality workout system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

The exemplary embodiments are directed to a method, computer program product, and system for determining an augmented reality (AR) workout based on a cognitive state of a user. As will be described in greater detail herein, the exemplary embodiments are configured to determine the current cognitive state of the user and incorporate various further information in determining the AR workout to be utilized for a current workout session where the further information may include predictive results based on historical information associated with the user and characteristic information of the user. The exemplary embodiments provide a mechanism to monitor the cognitive state of the user during the AR workout such that the AR workout may be modified dynamically in real time based on changes to the cognitive state of the user. Key benefits of the exemplary embodiments may include providing an AR application that is dynamic and customized to improve the user's overall workout success, particularly based on the user's cognitive state to reduce stress levels. Detailed implementation of the exemplary embodiments follows.

Conventional approaches to providing a workout application that incorporate virtual components rely on rules based formulas to display the virtual components to a user. For example, conventional approaches may provide a visually virtual workout in which video programming is shown by selecting various parameters (e.g., a mode, a speed, a scene, etc.) or provide a real time simulation by dynamically varying a resistance setting of the exercise equipment. However, such conventional approaches are essentially linear with regard to a sequence of how the virtual components or simulations are displayed or performed, respectively, relying only on the program itself. In another example, conventional approaches may utilize a feedback to show a user's progress from previous workouts or gauge fitness progression by allowing the user to virtually compete against past performances or other users. However, such conventional approaches are also essentially linear without consideration of current circumstances of the user, particularly a cognitive state. In a further example, conventional approaches may create a virtual workout experience for a user where the experience may attempt to assist or motivate the user through various regimens, may create a shared workout experience for a plurality of users, may provide a virtual personal trainer, may create a themed virtual reality environment, etc. However, again, these conventional approaches are essentially linear without consideration of current circumstances of the user, particularly a cognitive state.

In contrast to conventional approaches, the exemplary embodiments may utilize AR technology in a dynamic and customized approach that recognizes that the cognitive state of the user may define the AR workout to be provided so that the workout session remains productive while also providing additional benefits associated with exercising. Accordingly, rather than simply generating a linear experience for the user, the exemplary embodiments may initially select the AR workout in a customized manner according to various personalized parameters of the user including a detected current cognitive state, predictive results based on historical information associated with the user, and characteristic information of the user that indicates a personality and/or personality traits of the user. The exemplary embodiments may also monitor the user during the workout session while utilizing the selected AR workout and provide modifications to the AR workout based on updated circumstances of the user, with a particular emphasis on the user's cognitive state.

The exemplary embodiments provide an AR workout system that correlates a contextual activity and a cognitive state of a user with a visual scene to be displayed on an AR headset such that virtual components are shown relative to real world surroundings. The exemplary embodiments may continuously understand a mood of the user via the cognitive state which provides a basis upon which to create a dynamic and custom user AR environment resulting in an improved motivational workout environment. The exemplary embodiments may also be modified to interlace two or more multi-user AR participants in an overall AR environment with customization based on each user's contextual activity and respective cognitive state. Furthermore, the exemplary embodiments may integrate an AR user experience utilizing workout equipment that is dynamically available and providing navigation from currently available equipment to a next piece of equipment as part of a user customized experience.

The exemplary embodiments are described with regard to a cognitive state of a user prior to starting an AR workout and during the AR workout in which the AR workout is selected and/or modified based on the cognitive state. However, the exemplary embodiments may be utilized and/or adapted to be used in determining and monitoring any aspect of a user utilizing the system as well as provide a corresponding output based on the aspect of the user.

FIG. 1 depicts an AR workout system 100, in accordance with the exemplary embodiments. According to the exemplary embodiments, the AR workout system 100 may include one or more smart devices 110 that may operate in conjunction with sensors 114 and an AR headset 116, one or more profile repositories 120, an AR server 130, and one or more characteristic repositories 140, which may all be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted.

In the exemplary embodiments, the network 108 may be a communication channel capable of transferring data between connected devices. Accordingly, the components of the AR workout system 100 may represent network components or network devices interconnected via the network 108. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a WiFi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices. For example, the network 108 may also represent direct or indirect wired or wireless connections between the components of the augmented reality workout system 100 that do not utilize the network 108.

In the exemplary embodiments, the smart device 110 may include a workout client 112 and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an Internet of Things (IoT) device, or any other electronic device or computing system capable of receiving and sending data to and from other computing devices. While the smart device 110 is shown as a single device, in other embodiments, the smart device 110 may be comprised of a cluster or plurality of computing devices, in a modular manner, etc., working together or working independently. The smart device 110 is described in greater detail as a hardware implementation with reference to FIG. 4, as part of a cloud implementation with reference to FIG. 5, and/or as utilizing functional abstraction layers for processing with reference to FIG. 6. Each of the one or more smart devices 110 may be used by a respective operator having a corresponding operator skill set used in resolving incidents arising at a client data center.

In the exemplary embodiments, the workout client 112 may act as a client in a client-server relationship and may be a software, hardware, and/or firmware based application capable of presenting the AR workout to the user via the network 108. In embodiments, the workout client 112 may operate as a user interface allowing the user to generate the virtual components of the AR workout while viewing real world surroundings as well as interact with one or more components of the AR workout system 100, and utilize various wired and/or wireless connection protocols for data transmission and exchange associated with utilizing the AR workout, including Bluetooth, 2.4 gHz and 5 gHz internet, near-field communication, Z-Wave, Zigbee, etc.

The workout client 112 may provide the user interface in cooperation with the AR headset 116 in presenting the AR workout with virtual components shown in relation to real world surroundings. Accordingly, the workout client 112 may generate the virtual components, process locations of items in the real world surroundings, and determine how to place the virtual components seamlessly with the real world surroundings (e.g., determine portions of virtual components that are visible, determine portions of virtual components that are occluded, etc.). Those skilled in the art will understand the various techniques that may be utilized in presenting an AR experience to a user. For example, the workout client 112 may generate one or more masks representative of the items in the real world surroundings to determine how to position and show the virtual components. The exemplary embodiments may be configured to utilize any of these techniques. As will be described in further detail below, the workout client 112 may exchange data with the AR server 130 that may be used in determining the AR workout to be presented to the user.

The workout client 112 may further be configured to present information that may be used for viewing by the user, as a prompt to provide information, etc. For example, via the user interface, the workout client 112 may provide information that may be used in determining which AR workout to be presented. The user may provide identification information that uniquely identifies the user. The smart device 110 and/or the AR headset 116 may include an input device (e.g., a keypad, a microphone, etc.) that allows the identification information to be provided to the workout client 112. When the AR headset 116 is only associated with a single user, the AR headset 116 may provide the identification information to the workout client 112. In another example, the workout client 112 may be configured to show the user a variety of options via the user interface. For example, when configured, the AR workout that is to be used may be presented as a selectable option. Thus, the workout client 112 may show one or more AR workouts to the user from which the user may select. In a further example, when configured, the workout client 112 may show results of completing the AR workout (e.g., distance traveled, calories burned, etc.).

The sensors 114 may generate various types of information associated with the user and/or the smart device 110. For example, the sensors 114 may include imagers and/or ultrasound sensors (e.g., transmitters and receivers). The imagers may generate image data of the real world surroundings around the user. The ultrasound sensors may generate ultrasound data to detect distances to objects in the real world surroundings from the user. The image data and/or the ultrasound data may also be used to detect changes in position over time of the objects in the real world surroundings around the user (e.g., based on changes from first data at a first time to second data at a second, subsequent time). In another example, the sensors 114 may include biometric sensors configured to detect biometric readings of the user (e.g., a heart rate monitor may determine a heart rate, a thermometer may determine a temperature, a blood pressure monitor may determine a blood pressure, a fitness tracker may determine calories burned/steps taken/etc., a timer may measure when the user is exercising or not, etc.). In a further example, the sensors 114 may include a location device such as a global positioning system (GPS) device configured to determine a position of the user in the real world surroundings. In yet another example, the sensors 114 may include movement sensors (e.g., an accelerometer, a gyroscope, etc.) configured to determine local movement being performed by the user or body parts of the user. In an additional example, the sensors 114 may include eyes trackers configured to determine a location that the user's eyes are focusing on an object in the real world surroundings and/or on a virtual component being shown. In yet another additional example, the sensors 114 may include a microphone configured to determine any auditory output from the user (e.g., breathing through nose or mouth, panting, speaking, etc.).

The AR headset 116 is described as a transparent lens that allows the user to view the real world surroundings and incorporate virtual components within a context of the real world surroundings. The AR headset 116 may also be a virtual reality headset in which the real world surroundings are incorporated in a virtual reality world presented via the virtual reality headset. In this manner, the AR workout may be presented in an entirely virtual reality world with a plurality of virtual components yet still utilize the real world surroundings to provide an AR experience.

The sensors 114 are shown as being separate from the smart device 110 and the AR headset 116 with a communications capability with the network 108. In this manner, as illustrated, the sensors 114 may be substantially separate and independent in operation with data exchange with the network 108 providing the outputs to the corresponding component of the AR workout system 100. However, the separate configuration is only for illustrative purposes. The exemplary embodiments may be configured in various other manners. According to another exemplary implementation of the exemplary embodiments, select ones of the sensors 114 may be incorporated in one or more of the components of the AR workout system 100. For example, the imagers and ultrasound sensors may be incorporated in the AR headset 116 such that outputs of the imagers and ultrasound sensors may correspond directly to a position of the AR headset 116 for virtual component processing and placement. In another example, the eye trackers may also be incorporated in the AR headset 116 as the user's eyes are in proximity to the AR headset 116 for viewing purposes. In a further example, the location device and the movement sensors may be incorporated in the smart device 110 or to a corresponding component worn by the user to measure changes in position. In yet another example, the biometric sensors may remain separate and positioned at corresponding locations on the body, limb, or head of the user to measure the respective biometric parameter (e.g., on a wearable device). The above described implementation is also only illustrative. Those skilled in the art will understand the various manners in which the sensors may be incorporated into other components and/or remain independent in a way that the appropriate output may be provided.

The AR headset 116 may be an AR compatible device in which the real world surroundings are visible and virtual components may be generated and displayed in an integrated manner with the real world surroundings. For example, the AR headset 116 may have a substantially eyewear shape with a lens section, temples extending therefrom for the AR headset 116 to be worn over the user's ears, and other parts that may provide comfort in wearing the AR headset 116. The lens section may include a display on which the virtual components are generated and shown. According to an exemplary embodiment, the display may be at least partially transparent for the real world surroundings to be visible through the display while the virtual components are presented on the display in a manner to be seamlessly integrated with the real world surroundings (e.g., incorporating depth considerations, adding shadows at the correct angle, etc.). However, the transparency is only exemplary and the AR headset 116 may be configured in other manners for the real world surroundings to be visible with the virtual components. For example, the display may be a conventional screen. However, the display may show the real world surroundings as a video (e.g., based on the cameras that capture the real world surroundings). The virtual components may be incorporated into the video so that the video is shown with the real world surroundings and the virtual components (e.g., generating a single video stream that combines the real world surroundings and the virtual components, generating two video streams that are rendered together for viewing, etc.).

The AR headset 116 is shown as being separate from the smart device 110 with a communications capability with the network 108. Thus, communications between the AR headset 116 and the smart device 110 may be performed via the network 108. As described above, the workout client 112 may render the AR workout for viewing on the AR headset 116. Therefore, the workout client 112 may transmit the corresponding data to the AR headset 116 via the network 108. However, the network communication between the AR headset 116 and the smart device 110 is only exemplary. According to another exemplary embodiment, the AR headset 116 may be directly connected to the smart device 110 (e.g., via a wired connection, via a near field communication (NFC) link, etc.). Therefore, the workout client 112 may communicate directly with the AR headset 116. In a further exemplary embodiment, the smart device 110 and the AR headset 116 may be parts of a common device. Accordingly, the components of the smart device 110 and the AR headset 116 may be integrate into one another in such a way that the user may comfortably utilize the combined device (e.g., form factor considerations).

In the exemplary embodiments, the profile repository 120 may include one or more user profiles 122 and may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of storing, receiving, and sending data to and from other computing devices. While the profile repository 120 is shown as a single device, in other embodiments, the profile repository 120 may be comprised of a cluster or plurality of electronic devices, in a modular manner, etc., working together or working independently. While the profile repository 120 is also shown as a separate component, in other embodiments, the profile repository 120 may be incorporated with one or more of the other components of the AR workout system 100. For example, the profile repository 120 may be incorporated in the AR server 130. Thus, access to the profile repository 120 by the AR server 130 may be performed locally. The profile repository 120 is described in greater detail as a hardware implementation with reference to FIG. 4, as part of a cloud implementation with reference to FIG. 5, and/or as utilizing functional abstraction layers for processing with reference to FIG. 6.

In the exemplary embodiments, the user profiles 122 may each be associated with a respective user who utilizes the AR workout system 100. The user profiles 122 may be populated with various types of information that may be used by the AR server 130 to determine the AR workout to be selected for the user. For example, each of the user profiles 122 may be associated with a user identification to uniquely identify one user from among a plurality of users. In another example, each of the user profiles 122 may include historical information with regard to previous workout sessions as well as all other information related to the previous workout sessions (e.g., day and time that a workout session was done, the type of workout, results of the workout session, times of activity and rest during the workout session, a selection of the AR workout prior to the user starting the workout session, changes to the selected AR workout during the workout session, a cognitive state at the start/during/end of the workout session, etc.). In a further example, when the sensors 114 are configured to monitor the user during durations outside of workout sessions, each of the user profiles 122 may include further historical information of wake periods, sleep periods, active periods, rest periods, etc. along with the cognitive state of the user at indicated timeframes throughout the day. In yet another example, the workout client 112 may include an option in which the user may provide personal and/or preference settings. The personal and/or preference settings may be included in the user profiles 122. The personal settings may include various measurements (e.g., height, current weight, desired weight, etc.), various personal information (e.g., a user schedule, demographics such as nationality, age, gender, etc., access to a gym and/or workout equipment, etc.), etc. The preference settings may include various subjective indications personal tastes (e.g., preferred times for a workout session, preferred types of workouts, preferred types of workouts to be omitted, etc.).

In the exemplary embodiments, the characteristic repository 140 may include one or more characteristic profiles 142 and may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of storing, receiving, and sending data to and from other computing devices. While the characteristic repository 140 is shown as a single device, in other embodiments, the characteristic repository 140 may be comprised of a cluster or plurality of electronic devices, in a modular manner, etc., working together or working independently. While the characteristic repository 140 is also shown as a separate component, in other embodiments, the characteristic repository 140 may be incorporated with one or more of the other components of the AR workout system 100. For example, the characteristic repository 140 may be incorporated in the AR server 130. Thus, access to the characteristic repository 140 by the AR server 130 may be performed locally. The characteristic repository 140 is described in greater detail as a hardware implementation with reference to FIG. 4, as part of a cloud implementation with reference to FIG. 5, and/or as utilizing functional abstraction layers for processing with reference to FIG. 6.

In the exemplary embodiments, the characteristic profiles 142 may each be associated with a respective user who utilizes the AR workout system 100. The characteristic profiles 142 may be populated with various types of information that may be used by the AR server 130 to determine a type of person that the user is. As will be described in further detail below, the AR workout may be customized to correspond to the user's characteristics (e.g., to maintain motivation throughout the AR workout). The user's characteristics may relate to personality traits, scenery preferences, subjective familiarity with persons/places/things, introversion/extroversion characteristics, general likes/dislikes, etc.

The characteristic profiles 142 may be based on a variety of different sources from which the user's characteristics may be determined. For example, when provided access (e.g., with security measures in place to ensure that the information is properly handled) or public information is available, the characteristic profiles 142 may be based on social media outlets. The characteristic profiles 142 may also be populated with information that is manually provided by the user (e.g., a personality test may be administered, a survey may be presented, etc.). The characteristic profiles 142 may further be populated with information included in the user profile 122. For example, the historical information included in the user profile 122 may provide insight on various personality traits (e.g., whether the user is prone to giving up quickly in the short term or over time).

In the exemplary embodiments, the AR server 130 may include a cognitive state program 132, an AR workout program 134, a monitoring program 136, and a predictive program 138 and act as a server in a client-server relationship with the workout client 112 as well as be in a communicative relationship with the sensors 114, the AR headset 116, the profile repository 120, and the characteristic repository 140. The AR server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the AR server 130 is shown as a single device, in other embodiments, the AR server 130 may be comprised of a cluster or plurality of computing devices, working together or working independently. While the AR server 130 is also shown as a separate component, in other embodiments, the operations and features of the AR server 130 may be incorporated with one or more of the other components of the augmented reality workout system 100. For example, the operations and features of the AR server 130 may be incorporated in the smart device 110, particularly the smart device 110 of the operator who is resolving an incident. The AR server 130 is described in greater detail as a hardware implementation with reference to FIG. 4, as part of a cloud implementation with reference to FIG. 5, and/or as utilizing functional abstraction layers for processing with reference to FIG. 6.

In the exemplary embodiments, the cognitive state program 132 may be a software, hardware, and/or firmware application configured to determine a cognitive state of the user. The cognitive state program 132 may receive the outputs from the sensors 114 that provide physical information of the user. Based on the physical information, the cognitive state program 132 may be configured to determine the cognitive state of the user through correlations of one or more physical descriptions to a plurality of cognitive states. Each of the cognitive states may have one or more thresholds for select ones of the physical descriptions. For example, the physical descriptions may be indicative of an aggression or frustration level or value. The cognitive state program 132 may be programmed with thresholds that identify when the aggression or frustration level satisfies a stress threshold to determine when the user is in a stressed state with a corresponding stressed cognitive state. In an implementation, the select physical descriptions may have respective physical values from which a comparison to the corresponding threshold is determined. The cognitive state program 132 may determine when a particular combination of satisfactions of the thresholds indicate a particular cognitive state to be recognized. In another exemplary implementation, the select physical descriptions may be combined to generate an overall physical value from which a comparison to an overall threshold is determined. The cognitive state program 132 may determine when the overall physical value falls within one of a plurality of threshold ranges where each threshold range is indicative of a respective cognitive state. As each person may be affected by physical descriptions differently than others, the cognitive state program 132 may set the thresholds in a customized and/or personalized manner specific to the user. For example, an initial exam or questionnaire may be administered to the user where the results may be used to determine the various thresholds. The examination of the user may be performed at subsequent times to dynamically set thresholds as the user may change over time. In a further example and according to an exemplary implementation, the cognitive state may be determined based on a cognitive score determined using the physical descriptions from outputs of the sensors 114. The cognitive score may be measured against a plurality of thresholds that indicate a level of stress being experienced by the user. The stress levels may range from entirely stress free to highly stressed (e.g., the stress levels may be ordered from 0 to 10 where 0 is indicative of a stress free cognitive state and 10 is indicative of a highly stressed state).

The cognitive state program 132 may determine a plurality of different cognitive states. For example, the cognitive state program 132 may determine when the user is happy, sad, stressed, relaxed, etc. The cognitive state program 132 may utilize a plurality of different manners in which to utilize the outputs of the sensors 114 in providing the physical descriptions to determine the cognitive state. Those skilled in the art will understand the various mechanisms that may be used. The exemplary embodiments may be configured to utilize any of these mechanisms.

The cognitive state program 132 may also be configured to utilize the sensors 114 to monitor the user during the AR workout. In receiving outputs from the sensors 114 during the AR workout, the cognitive state program 132 may determine an update to the cognitive state of the user. For example, the update to the cognitive state of the user (e.g., an active cognitive state during a time duration when the AR workout is being utilized) may indicate a motivation in continuing the AR workout as is, a satisfaction of the AR workout, etc. Changes or stagnation to the cognitive state may be provided to, for example, the AR workout program 134 so that an appropriate action may be performed. The cognitive state program 132 may also determine whether each of the physical descriptions match a respective expected physical description. For example, the user may be performing the AR workout but the physical descriptions are falling under the expected physical descriptions (e.g., pace is not as high, intensity of the user is waning, etc.). The cognitive state program 132 may utilize such parameters in determining the changes to the cognitive state. The cognitive state program 132 may also directly report the physical descriptions along with any comparison to a corresponding threshold (e.g., expected physical description).

In the exemplary embodiments, the AR workout program 134 may be a software, hardware, and/or firmware application configured to determine the AR workout for the user to perform based on the cognitive state of the user and incorporating other factors such as information from the user profile 122 of the user and the characteristic profile 142 of the user. The AR workout program 134 may be programmed with a plurality of different AR workouts. Each of the AR workouts may have baseline features from which a specific AR workout selected for a user may be customized or personalized. For example, the AR workout may be a running workout session. The AR workout program 134 may customize the running workout session in a variety of manners to provide the user with a customized experience according to the various considerations such as a background, a scenery, a competition with one or more runners, a solo adventure, a course, etc. In another example, the AR workout may be a weight lifting workout session. The AR workout program 134 may customize the weight lifting workout session in a variety of manners to provide the user with a customized experience according to various considerations such as one or more target muscle groups, consideration of others utilizing equipment, available equipment, purpose of weight lifting (e.g., toning, bulking, etc.), etc. In this manner, the AR workout program 134 may tailor the AR workout specifically for the user.

In customizing the AR workout, the AR workout program 134 may also consider additional factors including the cognitive state of the user, the historical information included in the user profile 122, and the characteristic information included in the characteristic profile 142. The AR workout program 134 may determine that the cognitive state of the user may be served with a particular type of AR workout. For example, the cognitive state program 132 may determine that the user is currently stressed. Thus, to relieve that stress and depending on the personality of the user, the AR workout program 134 may determine that a corresponding workout session be provided (e.g., an alpha personality may warrant a faster running pace at a shorter duration, heavier weights, etc. whereas a generally calmer personality may warrant a light jog through a serene backdrop for a longer duration, a meditative yoga session, etc.). As already indicated, the AR workout program 134 may further incorporate the user's characteristic information as a first type of personality under determined cognitive state may utilize one manner of AR workout while a second type of personality under the same determined cognitive state may utilize a different manner of AR workout. Furthermore, the AR workout program 134 may utilize the historical information to determine the AR workout such as varying the workout from a prior one or more workout sessions (e.g., selecting a different type of workout), selecting a workout that had a positive result for the same cognitive state, providing relaxation for target muscle groups that were recently rigorously exercised, etc.

In addition to the above factors, the AR workout program 134 may identify the available AR workouts for the user. The AR workout program 134 may determine the available AR workouts on a high level or on a granular level. For example, at a high level, the AR workout program 134 may be aware that the user has a membership or access to a gym that has known equipment. In another example, at a granular level, the AR workout program 134 may determine the available equipment that is currently not in use by others. In a further example, the AR workout program 134 may determine a geographic location of the user to determine areas in which the user may exercise within a predetermined vicinity of the geographic location. The AR workout program 134 may consider each of these factors in a holistic manner to provide a specifically customized AR workout for the user in a solo capacity, as a competitive capacity with virtual components, as a group activity with other users and/or virtual components, etc. As will be described in detail below, select exemplary implements of AR workouts will be described.

Furthermore, the AR workout program 134 may receive results from the predictive program 138 that may provide insight as to the AR workout to be selected for the user. As will be described in detail below, the predictive program 138 may utilize the historical information of the user profile 122 to determine a prediction for various parameters of the AR workout (e.g., when to provide the AR workout, the type of AR workout to be provided, etc.). According to an exemplary implementation, the AR workout program 134 may utilize the results of the predictive program 138 when the user is not experiencing an anomalous cognitive state. For example, when the user is going through a day in a predictable manner based on the historical information, the AR workout program 134 may utilize the results from the predictive program 138. In a particular implementation, the historical information may provide a predictive cognitive state. When the cognitive state of the user corresponds to the predictive cognitive state within a difference threshold, the AR workout program 134 may incorporate the results of the predictive program 138. However, on any given moment of any given day, the user may be experiencing a cognitive state that may lie outside a substantially normal or predictable pattern. Accordingly, the AR workout program 134 may determine that the predictive cognitive state and the cognitive state of the user is greater than the difference threshold which is indicative of a pattern that does not correspond to the historical information. For example, the user may have a deadline at work that is increasing an amount of stress being experienced. In another example, the user may be participating in an exciting activity that changes the mood of the user relative to the historical information. Therefore, the AR workout program 134 may determine that the results of the historical information may be omitted in such cases where the difference threshold is not satisfied.

The AR workout program 134 may determine the AR workout based on the cognitive state in a variety of manners. According to an exemplary implementation, the AR workout program 134 may receive an indication that the user wishes to exercise (e.g., a manual input from the user, based on a schedule that the user follows, etc.). Based on the upcoming workout session, the AR workout program 134 may determine the cognitive state of the user and proceed to determining the AR workout for the workout session. In another exemplary implementation, when the sensors 114 are properly configured (e.g., being worn), the AR workout program 134 may continuously monitor the cognitive state of the user. When the cognitive state of the user is determined to be a predetermined cognitive state in which a workout session is to be performed, the AR workout program 134 may proceed to determining the AR workout for the determined cognitive state. In this manner, the AR workout program 134 may be configured to be a reactive program, a proactive program, or a combination thereof.

In the exemplary embodiments, the predictive program 136 may be a software, hardware, and/or firmware application configured to analyze the historical information and incorporate other factors to implicitly and/or explicitly learn patterns or behaviors of the user to more accurately determine the AR workout for subsequent workout sessions. The predictive program 136 may utilize a deep learning engine that learns correlations across a user's activity, user profile 122, characteristic profile 142, cognitive state, results of AR workouts that are determined by the AR workout program 134, etc. The predictive program 136 may apply the deep learning engine over a historical time window (e.g., n prior days including the current day). In this manner, the predictive program 136 may subsequently predict or generate an estimate of a user's cognitive state on the $n+1^{th}$ day or any future day.

The predictive program 136 may generate a model that is configured to capture a plurality of factors in predicting the user's cognitive state at a subsequent time. For example, the model may capture how the user may feel on a day, given a past mood or profile history as a time series of data points. In another example, the model may identify whether a suggested workout has been up to a user satisfaction level. In this manner, the predictive program 136 may generate the model to capture correlations across several different feature vectors (e.g., created from user activity logs, profile, etc.) as well as capture time dependencies across a period of time (e.g., several days). The model generated by the predictive program 136 may recognize correlations of cognitive states over time (e.g., how a user is feeling today may have some correlation on how the user is feeling tomorrow, a user may feel especially low on a given day of the week such as Monday morning or an individual who is single may feel lonely on a Friday evening, etc.). The predictive program 136 may therefore incorporate features in the deep learning architecture that is centered around, for example, a recurrent neural network. For example, the predictive program 136 may incorporate a layer that maps various features from the user profile 122 including any activity logs, the cognitive state determined by the cognitive state program 132, etc. which is embedded into the neural network. In another example, the predictive program 136 may incorporate a layer comprising of long short term memory (LSTM) units to handle the notion of sequential data over the past n days or other predetermined timeframe. Accordingly, after the predictive program 136 has been in use for a sufficient amount of time (e.g., when a determination is made that there is a threshold number of data points to learn weights across the model over the predetermined timeframe), the predictive program 136 may be configured to start predicting the user's cognitive state for next day or some future day or time. Based on the prediction, the predictive program 136 may provide an output to the AR workout program 134 to further customize the AR workout that is selected for the user. The predictive program 136 may track a satisfaction of the user for the AR workouts that are determined until a prediction for the following time shows an upward (e.g., positive) trend in satisfaction. However, as described above, the AR workout program 134 may also be configured to initially determine whether the output of the predictive program 136 is to be considered based on the difference threshold between the predicted cognitive state and a current cognitive state.

The above description is directed to an exemplary implementation utilizing network and/or nearfield communication (NFC) protocols in which data is exchanged among the various components of the AR workout system 100. For example, as noted above, the sensors 114 and the AR headset 116 may utilize NFC protocols while being in proximity to the smart device 110 or may exchange data with the smart device 110 via the network 108. In another example, the smart device 110 may be configured to utilize a network connection to exchange data with the AR server 130 that may include data from the sensors 114 and the AR headset 116. However, the use of the network and/or the NFC protocols is only exemplary. According to another exemplary implementation, the components of the AR workout system 100 may be incorporated in the smart device 110 where at least a portion of the data exchange is performed locally within the smart device 110. For example, the AR workout system 100 may be entirely incorporated in the smart device 110. In such an embodiment, the AR workout system 100 may be for a single user or set of users who may utilize the incorporated device.

Figure 2:
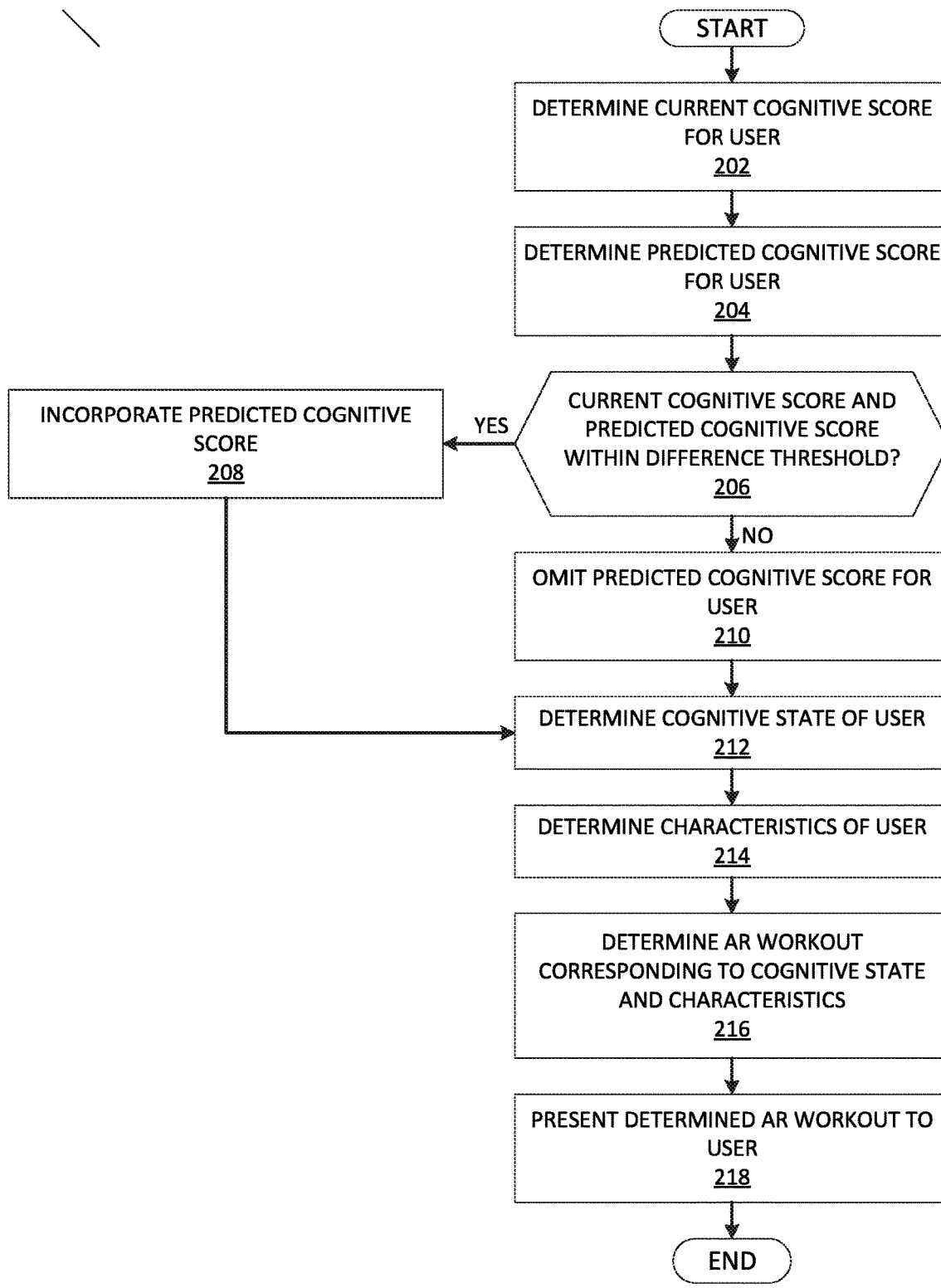
FIG. 2 depicts an exemplary flowchart of a method illustrating the operations of an augmented reality server 130 of the augmented reality workout system 100 in determining an augmented reality workout for a user, in accordance with the exemplary embodiments.

FIG. 2 illustrates an exemplary flowchart of a method 200 illustrating the operations of AR server 130 of the AR workout system 100 in determining an AR workout for the user, in accordance with the exemplary embodiments. The method 300 may relate to operations that are performed by the cognitive state program 132, the AR workout program 134, and the predictive program 136 to determine the most appropriate AR workout under the current circumstances surrounding the user regarding the user's cognitive state and other available information. The method 200 will be described from the perspective of the AR server 130.

Initially, as described above, the exemplary embodiments may be performed in a reactive manner or a proactive manner. In the reactive manner, the user may provide an indication and/or the AR workout system 100 (e.g., the AR workout program 134) may be configured to determine when the user will perform a workout session. Accordingly, based on this input and/or determination, the AR workout system 100 may reactively perform the method 200. In the proactive manner, the AR workout system 100 (e.g., the cognitive state program 132) may monitor the cognitive state of the user. When the cognitive state of the user corresponds to a predetermined cognitive state in which the user is to be provided the AR workout, the AR workout system 100 may proactively perform the method 200. The method 200 is applicable to either scenario with minor modifications or inclusions of additional steps.

The AR server 130 may determine a current cognitive score for the user (step 202). In ultimately determining the cognitive state of the user, the AR server 130 (e.g., via the cognitive state program 132) may receive outputs from the sensors 114 indicating physical descriptions of the user. Based on the physical descriptions, the AR server 130 may determine a cognitive score for the user. The cognitive score may be an overall score or a plurality of different scores based on one or more physical descriptions. For example, elevated biometric readings of pulse, heartrate, temperature, etc. may indicate that the user is in a stressed cognitive state. The AR server 130 may analyze the physical descriptions in an individual capacity when generating a plurality of cognitive scores or holistically when generating an overall cognitive score. Individually, the physical representations may have corresponding thresholds or range of thresholds such that a comparison may result in an individual cognitive score. Holistically, the physical representations may be considered as a combination which is compared to a range of thresholds, the result providing the overall cognitive score.

The AR server 130 may determine a predicted cognitive score for the user (step 204). In determining the AR workout for the user, the AR server 130 may incorporate historical information. For example, the AR server 130 may include an implicit and/or explicit learning based on a deep learning neural network architecture (e.g., via the predictive program 136) as utilized by a deep learning engine. Through the deep learning engine, the AR server 130 may identify various correlations of the user's cognitive state over time and how a prior cognitive state may predict a current cognitive state. The predictive cognitive state may provide insight as to the AR workout that is to be selected. Accordingly, the AR server 130 may determine the predicted cognitive score that may be incorporated in the determination of the AR workout that is determined.

The AR server 130 determines whether the predicted cognitive score and the current cognitive score are within a difference threshold (decision 206). Although the predictive cognitive score may be at least partially used in determining the AR workout, the predictive cognitive score is based on historical information as included in the user profile 122. When the user experiences conditions outside normal or expected conditions, there are opportunities for the current cognitive score to be significantly different than the predicted cognitive score. Therefore, the AR server 130 may be configured to incorporate the predicted cognitive score when the predicted cognitive score is determined to fall within the difference threshold relative to the current cognitive score (e.g., based on an assumption that the surrounding conditions are substantially similar when the cognitive scores are determined). Thus, as a result of the predicted cognitive score and the current cognitive score being within the difference threshold (decision 206, "YES" branch), the AR server 130 may incorporate the predicted cognitive score in subsequent processing (step 208). However, as a result of the predicted cognitive score and the current cognitive score being outside the difference threshold (decision 206, "NO" branch), thereby indicative of unique circumstances at the time the current cognitive score is determined, the AR server 130 may omit the predicted cognitive score in subsequent processing (step 210).

Based on the cognitive scores that are to be used, the AR server 130 may determine the cognitive state of the user (step 212). For example, the AR server 130 (e.g., via the cognitive state program 132) may utilize the results of the cognitive score and identify a threshold or threshold range in which the cognitive score corresponds where each threshold or threshold range is indicative of a cognitive state. The threshold or threshold ranges may be determined according to a customized predetermination for the user (e.g., based on preliminary information received from the user). In an alternative exemplary implementation, the AR server 130 (e.g., via the predictive program 136) may utilize historical information to automatically determine the thresholds or threshold ranges. Accordingly, after sufficient information is available, the AR server 130 may make these determinations. The AR server 130 may determine from a plurality of cognitive states (e.g., happy, sad, relaxed, stressed, etc.). In another exemplary embodiment, the AR server 130 may utilize a single threshold to determine whether the cognitive state falls on one side of the threshold (e.g., a state where the AR workout is to be used) or the other side of the threshold (e.g., a state where the AR workout is not to be used).

The AR server 130 may utilize further information in determining the AR workout to be utilized for the user. Thus, in one type of further information, the AR server 130 may determine characteristics of the user (step 214). For example, the AR server 130 may utilize the characteristics profile 142 of the user that provides information regarding a personality type, preferences, etc. In another example, the AR server 130 may utilize the user profile 122 of the user that provides other information regarding historical workout sessions, indicated preferences to selected AR workouts, etc.

Based on the cognitive state of the user (e.g., which may or may not include the predictive cognitive score/state which is based on historical information) and the characteristics of the user, the AR server 130 may determine the AR workout to be utilized by the user (step 216). The AR server 130 may then present the determined AR workout to the user (step 218). For example, when the cognitive state of the user is identified as one of a stressed condition and the user has characteristics that indicate a preference for rigorous competition to relieve that stress, the AR server 130 may select the AR workout as a sprint with a virtual runner (e.g., an adversary). The AR server 130 may present the determined AR workout to the user in a variety of manners. For example, according to a first configuration, the AR server 130 may present the determined AR workout as a recommendation. If properly selected, the user has an increased probability of accepting the determined AR workout. In another example, according to a second configuration, the AR server 130 may receive a setting that when the user requests the AR workout, the AR server 130 performs the method 200 to determine and provide the AR workout.

Figure 3:
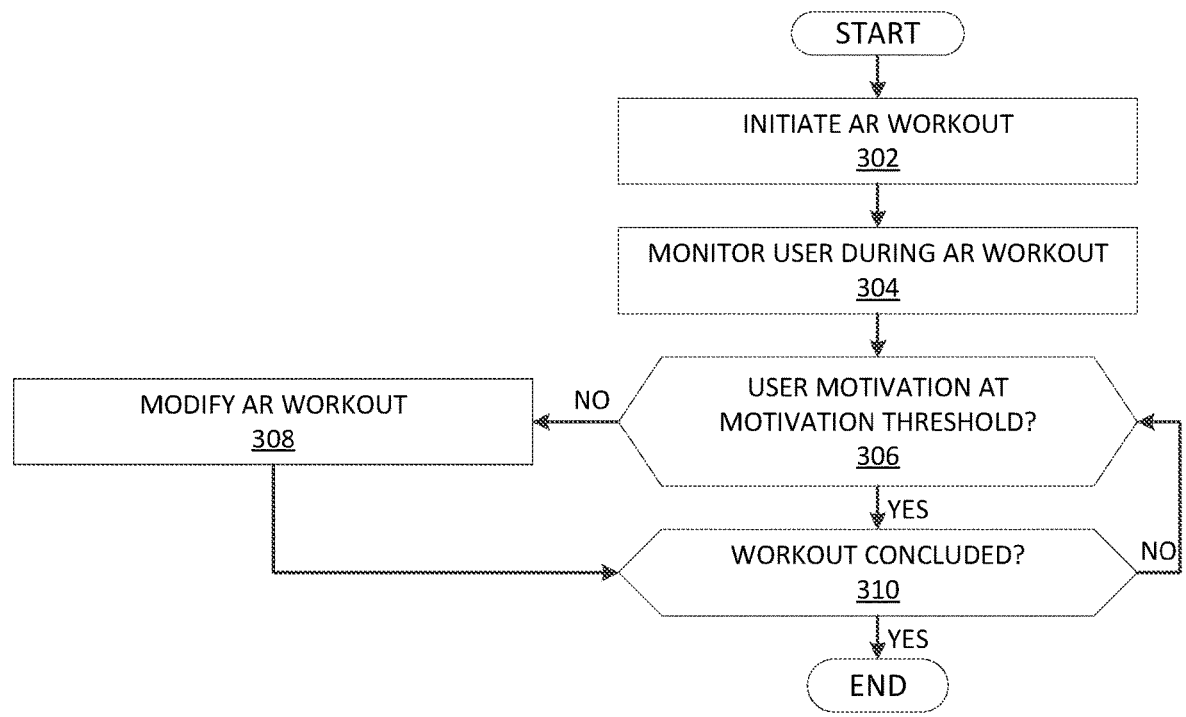
FIG. 3 depicts an exemplary flowchart of a method illustrating the operations of the augmented reality server 130 of the augmented reality workout system 100 in dynamically modifying the augmented reality workout for the user, in accordance with the exemplary embodiments.

FIG. 3 depicts an exemplary flowchart of a method 300 illustrating the operations of the AR workout system 100 in dynamically modifying the AR workout for the user, in accordance with the exemplary embodiments. The method 300 may relate to operations that are performed by the cognitive state program 132 and the AR workout program 134 to determine whether a currently selected AR workout is providing an appropriate experience for the user while the user is utilizing the AR workout. The method 300 will be described from the perspective of the AR server 130.

The AR server 130 may initiate the AR workout (step 302). After the AR workout is presented to the user (e.g., as an automated execution, as a recommendation that is accepted, etc.), the AR server 130 may begin providing the AR workout in which virtual components are incorporated into the real world surroundings. For example, the AR workout may be a personal trainer workout session where the user is lifting weights and the virtual personal trainer is positioned to appear nearby the user. The virtual personal trainer may be instructing the user as to proper form and technique for various weight lifting exercises.

When the AR workout has begun, the AR server 130 may begin monitoring the user (step 304). For example, the AR server 130 (e.g., via the cognitive state program 132) may continue to receive outputs from the sensors 114. The AR server 130 may determine whether the cognitive state of the user has been affected through changes to the cognitive score. In particular, the AR server 130 may determine whether the user is being motivated (e.g., at a motivation threshold), wants to continue with the determined AR workout, etc. (decision 306). For example, the AR server 130 may determine that the user is not maintaining a selected pace of the AR workout which may be indicative of the user being unmotivated with the AR workout. In another example, the AR server 130 may determine that the user is visually focusing on other areas rather than the virtual components designed to keep the user's focus. In customizing the AR workout for the user, the AR server 130 may monitor the user to ensure that user remains willing to want to continue the AR workout. In this manner, the AR server 130 may dynamically customize the AR workout in a manner that allows for the most efficient workout session.

As a result of the AR server 130 determining that the AR workout is not satisfying the motivation threshold (decision 306, "NO" branch), the AR server 130 may modify the AR workout (step 308). For example, the AR server 130 may have determined that at a previous time, the determined AR workout had a positive result from the user utilizing the determined AR workout. However, the user's feelings may have changed regarding this determined AR workout where the user is finding that the determined AR workout is identical or too similar to the prior workout and is finding the determined AR workout to be boring. In another example, the user may have initially been excited about the AR workout but, over time, finds that the AR workout is no longer providing the proper stimulation. Accordingly, the AR workout may automatically or recommend that a change to the determined AR workout or an entirely different AR workout be utilized. The AR server 130 may utilize the operations of the method 200 to determine the manner in which the modify the AR workout. Thereafter, the AR server 130 may determine whether the AR workout is completed (decision 310).

As a result of the AR server 130 determining that the AR workout is satisfying the motivation threshold (decision 306, "YES" branch), the AR server 130 may continue to provide the determined AR workout. Thereafter, the AR server 130 may determine whether the AR workout is completed (decision 310).

As a result of AR workout still ongoing (decision 310, "NO" branch), the AR server 130 may continue to monitor whether the determined AR workout provides sufficient motivation to satisfy the motivation threshold (decision 306). This process may be iterative so long as the AR workout is being utilized. In this manner, the AR server 130 may continuously customize the AR workout for the purposes of the user in an ad hoc approach that fits the immediate needs of the current workout session. For example, the initially determined AR workout may be further customized utilizing these operations. In another example, a modification of the determined AR workout may be further modified and so forth to provide customization through these operations. As a result of the AR workout being complete (decision 310, "YES" branch), the AR server 130 may conclude the AR workout. Upon completion, the AR server 130 may perform further operations (not shown). For example, the AR server 130 may continue receive outputs from the sensors 114. By measuring biometric readings of the user after completion of the AR workout, the AR server 130 may update the user profile 122 with results of the one or more determinations of the AR workouts. The predictive program 136 may thereby utilize further information as well as move the window for the LSTM. In another example, the AR server 130 may present a questionnaire for which the user may provide direct responses with regard to the one or more determinations of the AR workouts.

To further illustrate the operations of the AR server 130 performing the methods 200 and 300, reference is now made to an illustrative exemplary embodiment. The illustrative exemplary embodiment is directed towards a particular example in which select types of operations (e.g., operations may be performed in a plurality of ways) are utilized. The illustrative exemplary embodiment will be described with regard to the steps of methods 200 and 300 and from the perspective of the AR server 130.

According to the illustrative exemplary embodiment, the AR server 130 may monitor various aspects of the user (e.g., the user schedule, GPS location, history of activity such as via the historical information included in the user profile 122, etc.) and determine a pattern to deduce or estimate that the user may be intending to engage in a workout session. As a separate implementation or in combination with this operation, the AR server 130 may also determine that the cognitive state of the user is not positive or otherwise indicative of recommending a workout session. For example, the cognitive state may be determined using a threshold and a determined cognitive score exceeding the threshold where the threshold may be derived and updated based on observations using the sensors 114, the cognitive state capable of being confirmed through prompting the user for confirmation of the determined cognitive state [e.g., "Are you stressed?"]. From this data, the AR server 130 may derive the threshold as to when the cognitive state is not considered positive.

In the illustrative exemplary embodiment, the AR server 130 may utilize any basis upon which to predict when the workout session is to be performed by the user (e.g., monitoring the cognitive state, predicting based on personal factors such as schedule, etc.). In a particular example, the AR server 130 may be dynamically monitoring the cognitive state of the user and determine that the cognitive state is not positive. Therefore, the AR server 130 may suggest that the user perform an AR workout to help improve the cognitive state of the user.

Continuing with the illustrative exemplary embodiment, the AR server 130 may utilize the sensors 114 (e.g., biometric sensors, a camera, an audio input/output device, a GPS tracker, movement sensors, etc.) to analyze the current cognitive state of the user and varied stress levels that the user may experience (e.g., based on varying threshold ranges over a spectrum of cognitive scores that indicate a relative aggression and/or frustration level) to determine the type of customization for the upcoming AR workout.

At some point in time prior to and/or concurrently with the current use of the AR server 130, the AR server 130 may have access to a characteristic profile 142 for the user where the characteristic profile 142 may be generated by the AR server 130 and/or be created by the user. The characteristic profile 142 may include various types of social data that is utilized in determining various characteristics of the user such as a personality type. The AR server 130 may be configured with various analysis operations (e.g., natural language processing) to analyze the social data and determine one of many user characteristics (e.g., does the user have an extroverted or introverted personality), level of compositeness, individuals with whom the user is associated, real or fictional individuals who may be considered a hero or a nemesis, etc.

Based on the cognitive state of the user and determining the characteristics about the user, the AR server 130 may define the type of suggested type of workout session and story line to be used in an AR workout. According to an exemplary implementation, the user may be competitive and may benefit from an AR workout in which the user runs a race against a real or fictional individual identified as a nemesis such as in a one-on-one/head-to-head race or as part of a group race. The AR server 130 may select the type of race based on the characteristics of the user such as selecting the two person race if the user is introverted or selecting the group race if the user is extroverted. According to another exemplary implementation, the user may not be very competitive to want to compete in a race with their nemesis to motivate them while also not being as social to some degree. The AR server 130 may instead select the AR workout by generating a motivational race by having a favorite hero run the race in a side-by-side way with the user in a more non-competitive manner (e.g., with an attitude to complete the race rather than winning the race) by including significant hero encouragement. In a further example, when the user is determined to be motivated based on competitive user characteristics, the AR server 130 may generate a virtual component of the nemesis in a customized manner such as making an avatar of the nemesis appearing in an improved or envious manner that the user may be motivated to strive to also appear (e.g., for this particular user, such a feature in the AR workout may provide additional motivation or a greater motivation than simply encouraging the user to win the race). In this manner, the AR server 130 may generate a virtual component of a corresponding individual or thing that may be customized to increase the motivation that matches the characteristics of the user.

The AR server 130 may generate a wide variety of different AR workouts based on the cognitive state of the user, the characteristics of the user, and any other available information (e.g., predictive information). The AR server 130 may also incorporate aspects that are in the real world surroundings around the user to determine the AR workout. For example, the user may be in a safe environment like a gym, a space within the user's home, etc. and may be using workout equipment where there is limited movement (e.g., a rowing machine, an elliptical machine, a spinning bike, stationary bike, etc.). The user may then wear the AR headset 116 which may include an audio output component. Alternatively, the AR headset 116 may be part of an AR system that includes a separate, wired audio output device, wireless external speakers, etc. The sensors 114 may begin to collect data from the user that may output biometric readings such as heart rate, movement, user orientation, etc.

The user is then presented with the AR workout in which virtual components are viewable within the space of the real world surroundings. For example, depending on the chosen AR workout as determined by the AR server 130, the user may be presented with a wildlife scenario where a pack of lions chases the user. The speed at which the lion chases the person may depend on the workout level which is based on the cognitive state of the user and/or the characteristics of the user. For example, an intense workout level may make the lions more aggressive and thus the user may be enticed to run harder and faster. For a moderate work-out level, the user may be presented with a scenario with slow and sickly lions and thus the effort to keep a distance from the lions may be significantly reduced.

In a particular manner of providing such a scenario, the user may visit a gym and wear the sensors 114 that may be non-obtrusive for purposes of performing the AR workout (e.g., the sensors 114 are worn on the user's hands and legs with the AR headset 116 worn on the user's head). The user may wear wireless Bluetooth earphones to receive audio outputs. All these devices may be wirelessly inter-connected. Before switching on the components local to the user, the user may hop onto the cross-trainer and, once settled into position, activate the AR headset 116 or otherwise initiate the AR workout while providing inputs as to the gym equipment being used for the AR workout. The user may also select the type of workout session with regard an intensity level (e.g., the user selects a "high intensity interval mode"). The user may then be presented with the AR workout as a scenario in the jungle with lions, rivers, tracks, grasslands, etc. As the user starts utilizing the gym equipment in an initial state (e.g., a walking phase), the user may view an avatar of the user walking in the jungle and hear sounds of the jungle via the earphones. The user may then hear the rumbling of a lion which comes through the earphones. The audio stimulus may then cause the user to look back and the lion (e.g., as a virtual component) may appear to approach the user. As a result, the user may begin increasing a pace (e.g., walk faster). As the lion further approaches, the user may attempt to outrun the lion, the pace of the runner being controlled via the pace of the lion being presented in the AR workout. This may be the high-intensive part of the AR workout. When the resting interval approaches for the AR workout, the user may look back to see that the lion is retreating or turning back from which the user may adjust the pace. The resting interval or cooldown portion may begin by presenting the user with a virtual tree with shade that indicates to the user that the pace may be slowed and the user may take a rest. The AR workout may conclude or may include further portions in which the chase may start again.

As noted above, the AR server 130 may also generate sections for the AR workout. For example, the AR server 130 may include an initial section of the AR workout in which preparations may be made (e.g., getting properly dressed for the type of workout session, stretching, etc.). In another example, the AR server 130 may include a workout section of the AR workout in which features such as those described above may be included. In a further example, the AR server 130 may include a cool down section of the AR workout when the exercise portion is completed. During the cool down section of the AR workout, the AR server 130 may generate a customized view that is presented to the user based on personal characteristics learned and constantly refreshed by social data learning (e.g., based on the characteristics profile 142 of the user). The customized view presented by the AR server 130 may include a relaxing environment of recent interest to a user (e.g., the user recently researched a trip to Hawaii) and provide the location specific sensory outputs (e.g., sights, sounds, smells, etc.). The AR server 130 may also provide the user a preferred relaxing music (e.g., learned from the user playing music at certain times such as bedtime or when participating in a relaxing activity). The AR server 130 may incorporate other customized features that may be presented during the cool down section of the AR workout.

In furtherance of the illustrative exemplary embodiment, during the AR workout, the AR server may monitor the cognitive state of the user and use the feedback from the sensors 114 to determine changes or stagnations to the cognitive state such as a change to the cognitive state that the user is not maintaining sufficient pace or intensity of the activity. As a result of such a determination, the AR server 130 may dynamically adjust the AR workout to increase the motivation of the user. For example, the AR server 130 may detect that the user motivation is waning. The AR server may then change the story line of the AR workout by determining (e.g., when inside a gym format where there are multiple pieces of equipment) which equipment is about to become or is available and then dynamically adjust the AR workout to present the user a new story line or make choices (e.g., by just moving along one or more pathways presented in the AR system). The user may follow the choice path which navigates the user to the next piece of available equipment (e.g., moving from a running platform to a climbing device) as the AR workout continues (e.g., in a seamless manner to appear as if the AR workout is proceeding as planned).

In a particular implementation, the AR server 130 may be utilized to present the AR workout for a single user in a solitary manner. However, in another implementation, the AR server 130 may be utilized so that a plurality of users may simultaneously participate in an AR workout (e.g., competitively, collaboratively, cooperatively, etc.). For example, the AR server 130 may navigate the users within a gym equipment space for the plurality of users all within the gym equipment space. Each of the users may be presented with an option to join the AR workout as a group. When more than one user selects to be part of the AR workout, the AR server 130 may generate the AR workout to include these users in, for example, an interlaced story made up where the users may share a common story line. From the perspective of a given user, the other users may be shown as virtual avatars visible to the given user where the avatars emulate the movements of the respective user within the gym equipment space.

In the illustrative exemplary embodiment, the AR server 130 may also perform further operations that may run in a background capacity (e.g., post processing while the user is not utilizing the features of the AR workout). For example, as described above, the AR server 130 may be configured with the predictive program 136 that implicitly and/or explicitly learns the patterns, behaviors, preferences, etc. of the user based on a deep learning neural network architecture. Thus, for each rendition of the AR workout, the AR server 130 may incorporate successes, failures, and other results in determining the AR workout for predictive purposes as well as other predictive parameters (e.g., predicting a likely user cognitive state to prepare to select the appropriate AR workout).

The AR server 130 generating the AR workout as a chase in the jungle by the lion may be one exemplary scenario that may be presented to the user. The AR server 130 may provide a variety of other scenarios that correspond to the cognitive state of the user and/or the characteristics of the user with various other customizations that may be utilized based on these and other factors (e.g., the real world surroundings). The following presents other scenarios that the user may utilize.

For example, the AR server 130 may generate the AR workout that recreates workout enhancing scenes or audio/visual effects in conjunction with virtual avatars for the user in the physical and/or virtual space where the AR workout is being performed. Based on the characteristics of the user, an avatar of the user that is viewable by the user may be embodied with a futuristic or a desired version of a body and/or body features that serve to motivate the user to attain the same body/features by visualizing the aggression level and "worked-out" carved body in virtual space in the form of self-reflection.

In another example, the AR server 130 may generate virtual components in the real world surroundings as virtual trainers to perform certain activities and instill aggression and confidence to the user while training based on an understanding of the user's cognitive state.

In a further example, the AR server 130 may modify the contextual situation by involving a social aspect of the AR workout where multiple users may be coordinating with each other or may visually inspect each other working out in a group setting to create further incentive for people who need companionship based motivation for enhanced adrenalin and heavy workouts. In addition, multiple users working out in a respective location may wear the AR headset 116 to visualize and coordinate with each other remotely instead of using dynamically created virtual avatars. In this manner, a plurality of users may utilize a common AR workout despite being separate from one another.

The exemplary embodiments are configured to generate an AR workout for a user based on a cognitive state of the user, characteristics of the user, historical and predictive information of the user, and any other information that may be available to provide a customized approach to generating the AR workout. In determining the cognitive state of the user to select the AR workout and customizing the AR workout based on the further information, the exemplary embodiments may dynamically determine the AR workout to be generated. In monitoring the cognitive state of the user during the AR workout, the exemplary embodiments may also dynamically modify the AR workout to match current circumstances surrounding the user's performance of the workout session.

Figure 4:
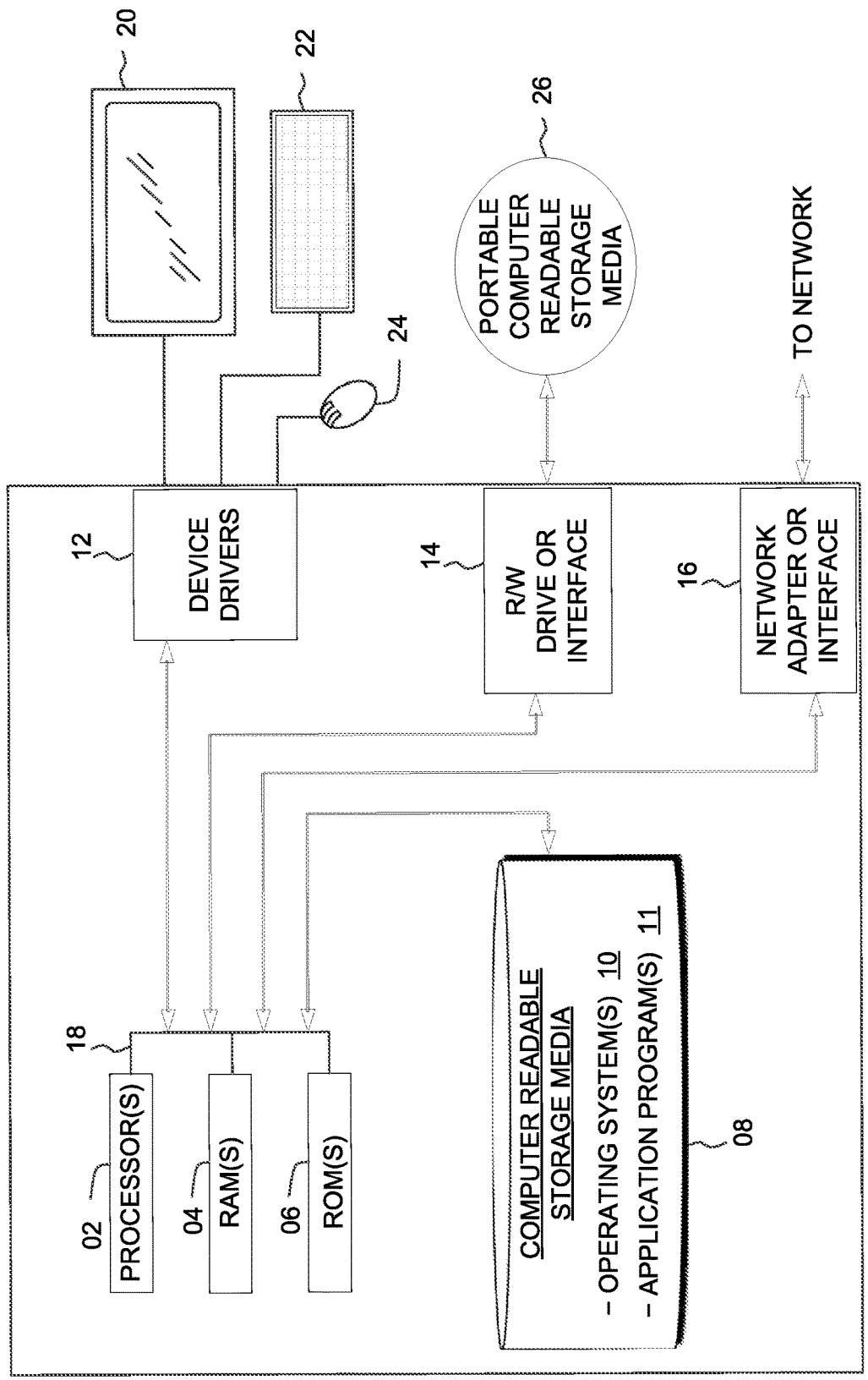
FIG. 4 depicts an exemplary block diagram depicting the hardware components of the augmented reality workout system 100 of FIG. 1, in accordance with the exemplary embodiments.

FIG. 4 depicts a block diagram of devices within the augmented reality workout system 100 of FIG. 1, in accordance with the exemplary embodiments. It should be appreciated that FIG. 4 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
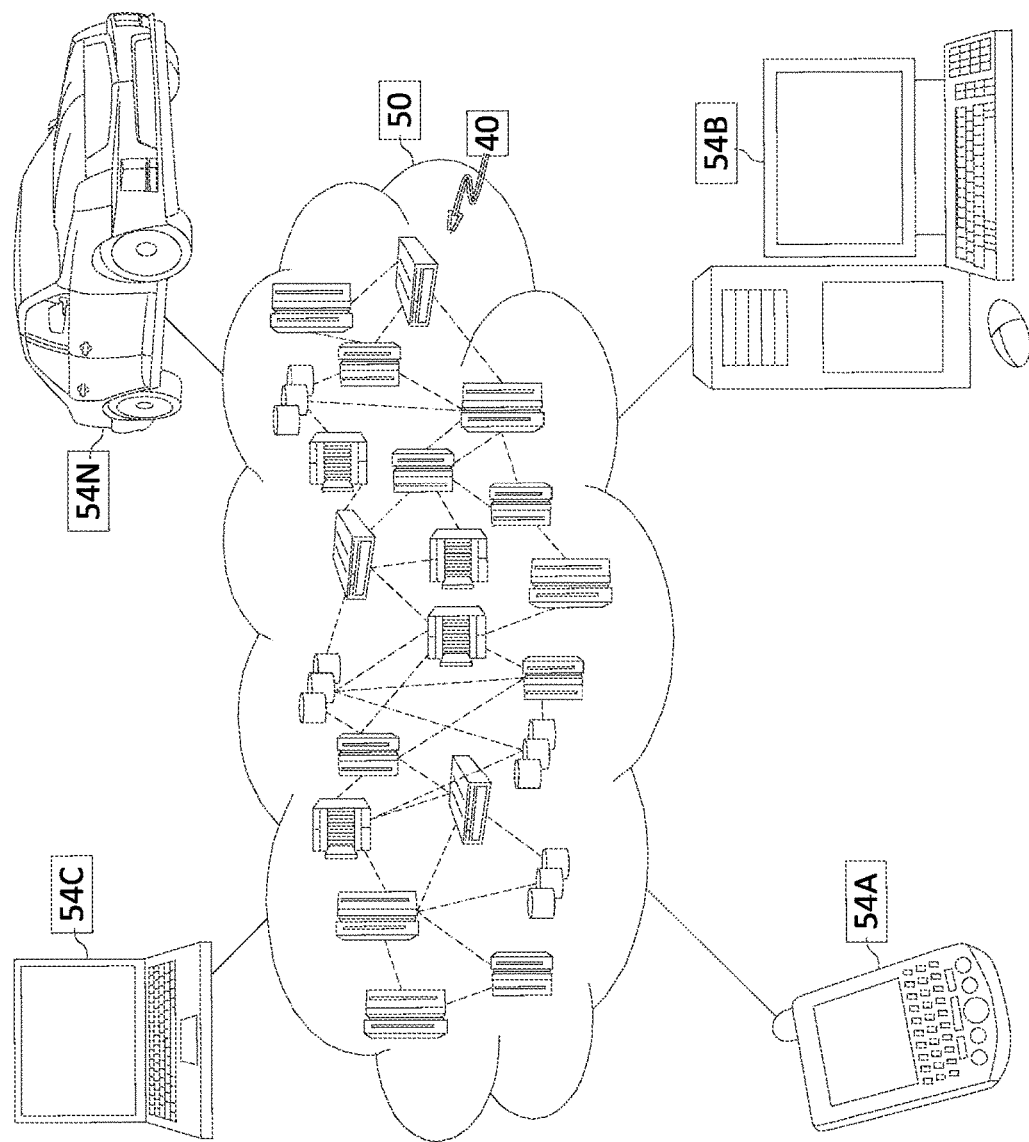
FIG. 5 depicts a cloud computing environment, in accordance with the exemplary embodiments.

Referring now to FIG. 5, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 40 and cloud computing environment 50 can communicate with any type of computerized device over any type of network and/or network addressable connection (e.g., using a web browser).

Referring now to FIG. 6, a set of functional abstraction layers provided by cloud computing environment 50 (FIG. 5) is shown. It should be understood in advance that the components, layers, and functions shown in FIG. 6 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and workout determination processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for determining a customized augmented reality (AR) workout based on a cognitive state of a user, the method comprising:
   determining a current cognitive score of the user based on physical descriptions;
   determining the cognitive state of the user based on the current cognitive score, the cognitive state being indicative of a stress level being experienced by the user;
   determining a storyline and type of the customized AR workout from a plurality of AR workouts based on the cognitive state of the user and one or more available pieces of equipment;
   generating the customized AR workout to include at least one virtual component and incorporating at least one feature of real world surroundings; and
   presenting the customized AR workout to the user via an AR device worn by the user.

2. The computer-implemented method of claim 1, further comprising:
   determining characteristics of the user, the characteristics being indicative of one of preference tastes, personality traits, or a combination thereof,
   wherein the customized AR workout is determined further based on the characteristics of the user.

3. The computer-implemented method of claim 1, further comprising:
   determining historical information of the user, the historical information being indicative of historical workout sessions utilizing historical AR workouts and corresponding historical cognitive states during the historical workout sessions; and
   wherein the customized AR workout is determined further based on the historical information.

4. The computer-implemented method of claim 3, further comprising:
   performing a deep learning operation on the historical information to determine correlations between the historical AR workouts and the historical workout sessions based on the historical cognitive states, the correlations indicative of a satisfaction level in being presented the historical AR workouts while experiencing the corresponding historical cognitive states.

5. The computer-implemented method of claim 1, further comprising:
   monitoring an active cognitive state of the user during a time duration that the user is utilizing the customized AR workout;
   determining whether the active cognitive state is at least a positive threshold, the positive threshold indicative of positive results from utilizing the customized AR workout; and
   as a result of the active cognitive state being below the positive threshold, modifying the customized AR workout based on the active cognitive state.

6. The computer-implemented method of claim 1, wherein the cognitive state is determined one of based on a manual indication for an upcoming workout session, based on a predictive indication for the upcoming workout session, or based on a monitoring of the physical descriptions of the user where the cognitive state is indicative of the stress level being above a stress threshold.

7. The computer-implemented method of claim 1, wherein the customized AR workout may be performed only the user or in one of competitively or collaboratively with at least one further user.

8. A computer program product for determining a customized augmented reality (AR) workout based on a cognitive state of a user, the computer program product comprising:
   one or more non-transitory computer-readable storage media and program instructions stored on the one or more non-transitory computer-readable storage media capable of performing a method, the method comprising:

determining a current cognitive score of the user based on physical descriptions;

determining the cognitive state of the user based on the current cognitive score, the cognitive state being indicative of a stress level being experienced by the user;

determining a storyline and type of the customized AR workout from a plurality of AR workouts based on the cognitive state of the user and one or more available pieces of equipment;

generating the customized AR workout to include at least one virtual component and incorporating at least one feature of real world surroundings; and presenting the customized AR workout to the user via an AR device worn by the user.

9. The computer program product of claim 8, wherein the method further comprises:

determining characteristics of the user, the characteristics being indicative of one of preference tastes, personality traits, or a combination thereof, wherein the customized AR workout is determined further based on the characteristics of the user.

10. The computer program product of claim 8, wherein the method further comprises:

determining historical information of the user, the historical information being indicative of historical workout sessions utilizing historical AR workouts and corresponding historical cognitive states during the historical workout sessions; and wherein the customized AR workout is determined further based on the historical information.

11. The computer program product of claim 10, wherein the method further comprises:

performing a deep learning operation on the historical information to determine correlations between the historical AR workouts and the historical workout sessions based on the historical cognitive states, the correlations indicative of a satisfaction level in being presented the historical AR workouts while experiencing the corresponding historical cognitive states.

12. The computer program product of claim 8, wherein the method further comprises:

monitoring an active cognitive state of the user during a time duration that the user is utilizing the customized AR workout;

determining whether the active cognitive state is at least a positive threshold, the positive threshold indicative of positive results from utilizing the customized AR workout; and as a result of the active cognitive state being below the positive threshold, modifying the customized AR workout based on the active cognitive state.

13. The computer program product of claim 8, wherein current cognitive state is determined one of based on a manual indication for an upcoming workout session, based on a predictive indication for the upcoming workout session, or based on a monitoring of the physical descriptions of the user where the cognitive state is indicative of the stress level being above a stress threshold.

14. The computer program product of claim 8, wherein the customized AR workout may be performed only the user or in one of competitively or collaboratively with at least one further user.

15. A computer system for determining a customized augmented reality (AR) workout based on a cognitive state of a user, the computer system comprising:

one or more computer processors, one or more computer-readable storage media, and program instructions stored on the one or more of the computer-readable storage media for execution by at least one of the one or more processors capable of performing a method, the method comprising:

determining a current cognitive score of the user based on physical descriptions;

determining the cognitive state of the user based on the current cognitive score, the cognitive state being indicative of a stress level being experienced by the user;

determining a storyline and type of the customized AR workout from a plurality of AR workouts based on the cognitive state of the user and one or more available pieces of equipment;

generating the customized AR workout to include at least one virtual component and incorporating at least one feature of real world surroundings; and presenting the customized AR workout to the user via an AR device worn by the user.

16. The computer system of claim 15, wherein the method further comprises:

determining characteristics of the user, the characteristics being indicative of one of preference tastes, personality traits, or a combination thereof, wherein the customized AR workout is determined further based on the characteristics of the user.

17. The computer system of claim 15, wherein the method further comprises:

determining historical information of the user, the historical information being indicative of historical workout sessions utilizing historical AR workouts and corresponding historical cognitive states during the historical workout sessions; and wherein the customized AR workout is determined further based on the historical information.

18. The computer system of claim 17, wherein the method further comprises:

performing a deep learning operation on the historical information to determine correlations between the historical AR workouts and the historical workout sessions based on the historical cognitive states, the correlations indicative of a satisfaction level in being presented the historical AR workouts while experiencing the corresponding historical cognitive states.

19. The computer system of claim 15, wherein the method further comprises:

monitoring an active cognitive state of the user during a time duration that the user is utilizing the customized AR workout;

determining whether the active cognitive state is at least a positive threshold, the positive threshold indicative of positive results from utilizing the customized AR workout; and as a result of the active cognitive state being below the positive threshold, modifying the customized AR workout based on the active cognitive state.

20. The computer system of claim 15, wherein the cognitive state is determined one of based on a manual indication for an upcoming workout session, based on a predictive indication for the upcoming workout session, or based on a monitoring of the physical descriptions of the user where the cognitive state is indicative of the stress level being above a stress threshold.

* * * * *